United States Patent [19]

Torosian

[11] Patent Number: 5,175,002
[45] Date of Patent: Dec. 29, 1992

[54] AMANTADINE HYDROCHLORIDE SYSPENSION WITH ENHANCED DISSOLUTION CHARACTERISTICS FOR USE IN SOFT GELATIN CAPSULES

[75] Inventor: George Torosian, Lynbrook, N.J.

[73] Assignee: Du Pont Merck Pharmaceutical Company, Wilmington, Del.

[21] Appl. No.: 770,461

[22] Filed: Oct. 2, 1991

[51] Int. Cl.$^5$ ............................................. A61K 9/64
[52] U.S. Cl. ................................ 424/456; 514/235.2; 514/255; 514/392; 514/647; 424/450
[58] Field of Search ................ 424/456, 450; 514/647, 514/235.2, 255, 392

[56] References Cited

U.S. PATENT DOCUMENTS

| | | | |
|---|---|---|---|
| 3,139,383 | 6/1964 | Neville | 424/462 |
| 3,310,469 | 3/1967 | Paulshock et al. | 514/23 |
| 4,241,047 | 12/1990 | Lechevin et al. | 424/451 |
| 4,350,679 | 9/1982 | Mizuno | 424/456 |
| 4,486,412 | 12/1984 | Shah et al. | 424/601 |
| 4,665,098 | 5/1987 | Gibbs et al. | 514/613 |
| 4,744,988 | 5/1988 | Brox | 424/456 |
| 4,812,481 | 3/1989 | Reischig | 514/647 |
| 4,822,629 | 4/1989 | Pong | 424/480 |
| 4,849,218 | 7/1989 | Hess et al. | 424/94.1 |
| 4,891,229 | 1/1990 | Brox | 424/456 |

FOREIGN PATENT DOCUMENTS 184942  8/1922  European Pat. Off. .

Primary Examiner—Thurman K. Page
Assistant Examiner—William E. Benston
Attorney, Agent, or Firm—Blair Q. Ferguson; Gildo E. Fato; Margaret A. Horn

[57] ABSTRACT

There are provided, novel no or low wax formulations for amantadine hydrochloride and methods for preparing such formulations.

25 Claims, No Drawings

AMANTADINE HYDROCHLORIDE SYSPENSION WITH ENHANCED DISSOLUTION CHARACTERISTICS FOR USE IN SOFT GELATIN CAPSULES

This is a division of application Ser. No. 07/543,602, filed Jun. 25, 1990.

FIELD OF THE INVENTION

This invention relates to improved formulations for water soluble compounds such as amantadine hydrochloride, particularly, formulations for amantadine hydrochloride, which, absent or with reduction of high melting point waxes, have significantly enhanced dissolution rates.

BACKGROUND OF THE INVENTION

Amantadine hydrochloride is a well known compound commercially available as Symmetrel ® from E. I. du Pont de Nemours and Company, Wilmington, Del. Available dosage forms of Symmetrel ® are soft gelatin capsules and oral syrup. U.S. Pat. No. 3,310,469 assigned to Du Pont, describes compositions containing amantadine.

Traditionally, when manufacturing oral pharmaceutical dosage forms such as soft gelatin capsules, for highly water soluble active ingredients, such as amantadine hydrochloride, the active ingredient is not dissolved but rather is suspended in a oleaginous mixture which is then used to fill the capsule. The suspensions used as fill material in the preparation of soft gelatin capsules must usually be sufficiently viscous to avoid the sedimentation of the suspended drug substance during the capsule filling. This process may take several hours. This fill variation is directly related to the dose variation from capsule to capsule and dependent upon the dynamic homogeneity of this suspension over the processing time.

Traditionally, the viscosity has been established with viscosity inducing agents either of mineral or vegetable origin such agents being either aqueous or oleaginous, such as: peanut, sesame, cottonseed, corn, sunflower, safflower, olive, and coconut oils, mineral oil, or waxes such as white wax, mono-, di-, triglycerides of edible oils, hydrogenated vegetable oil, beeswax, synthetic waxes of polyethylene glycol or their fatty acid esters. For examples of pharmaceutical compositions containing such viscosity inducing agents in soft gelatin capsules see: EP 184,942 which describes vitamin A soft gelatin capsules filled with wax mixtures in which active drug is suspended; and GE 1,282,853 which describes improved preparations for chloramphenicol suspended in a wax mixture of beeswax, hydrogenated soybean oil and hydrogenated vegetable oil.

In the case of Symmetrel ® which has been commercially available from Du Pont, the innovator, for many years, soft gelatin capsules have always contained in addition to the soybean oil suspending vehicle, high melting point waxes and lipid employed as viscosity inducing agents. These waxes and lipids, in addition to inducing viscosity are water insoluble and coat the otherwise water soluble amantadine hydrochloride, reducing its rate of dissolution in aqueous media. Now, surprisingly, it has been found that in the case of Symmetrel ®, a viscosity inducing agent is not required and the elimination or reduction of the high melting point waxes or substitution in part with low melting point lipids significantly enhances the dissolution rate. Surprisingly, the content uniformity is maintained in the absence or reduction of these high melting point waxes or with the substitution in part with low melting point lipids.

SUMMARY OF THE INVENTION

The present invention comprises no or low wax dosage forms of amantadine hydrochloride, such dosage forms having enhanced dissolution rates as well as appropriate content uniformity.

As used herein "no wax" means a suspension used to fill a capsule, wherein the amantadine hydrochloride is suspended in a vehicle containing no wax at all, either high melting point or low melting point waxes or lipids.

As used herein "low wax" means a suspension used to fill a capsule, wherein the amantadine hydrochloride is suspended in a mixture with low melting point wax or lipid (or a combination thereof) equalling no greater than 10% of the capsule fill weight or about 20.7 mg/capsules of a wax or lipid, and contains no high melting point waxes or lipids.

As used herein "high melting point wax or lipid" means lipid or oleaginous substances which are solids at room temperature and higher temperatures of about >45° C.-50° C.

As used herein "low melting point wax" means lipid or oleaginous substance which are a semi-solids at room temperature and melt at relatively low temperatures of about <45° C.-50° C.

DETAILED DESCRIPTION OF THE INVENTION

The pharmaceutical compositions of the invention a suspension of the following components:
  (a) a therapeutically effective amount of amantadine hydrochloride;
  (b) a no wax containing, suspending vehicle;
  (c) at least one emulsifying agent; and
  (d) optionally additional excipients.

Another embodiment of the invention comprises a suspension of the following components:
  (a) a therapeutically effective amount of amantadine hydrochloride;
  (b) a suspending vehicle comprising no greater than 10% of the capsule fill weight or 20.7 mg/capsule of a low melting point wax or low melting point lipid or a combination of low melting point waxes and/or lipids in addition to the primary vehicle;
  (c) at least one emulsifying agent; and
  (d) optionally additional excipients.

Amantadine hydrochloride may be prepared as known in the art, e.g., as described in U.S. Pat. No. 3,310,469.

Suspending vehicles/agents are used in suspensions in order to prevent the separation of the vehicle from the solid by the settling of the solid and to maintain the dynamic homogeneity prior to, and during the encapsulation process. These types of vehicles are well known in the art. The nature and concentration of the suspending agent will vary, depending on several factors, for example, the concentration of suspending agent must meet both the requirement for a physically stable suspension and the requirement for the mixture to have the proper flow characteristics, also, the suspending vehicle may act to coat the suspended solids imparting a certain lubricity to them that aids in encapsulation. Suspending vehicles useful in the present invention include but are not limited to soybean oil, peanut oil, sesame oil, cottonseed oil, corn oil, sunflower, olive oil, safflower oil and coconut oil.

In the low wax formulations of the present invention, any wax, or low melting point lipid present in the formulation, is present in an amount no greater than about 10% of the capsule fill weight or 20.7 mg/capsule and preferably is present in an amount no greater than 3.86% of the capsule fill weight or 8 mg/capsule. Examples of such waxes which may be used in the low wax formulation of the present invention include but are not limited to vegetable shortening, cocoa butter, margarine, Hard fat NF, butter, and partially hydrogenated vegetable oils.

Emulsifying agents are known to those skilled in the art who will appreciate that the nature and concentration of emulsifying agent used is dependent on many factors including, active ingredient, viscosity of the vehicle, desired release of the active ingredient etc. Examples of suitable emulsifying or wetting agents for use in the present invention include but are not limited to lecithin, polysorbate 20, 40, 60 and 80.

For the no wax formula the normal dose of amantadine hydrochloride is 100 mg. Component (b) the suspending vehicle, is used in the invention in a weight ratio relative to the amantadine hydrochloride of about 0.75 to 1.28 and preferably about 1.07, suspending vehicle/amantadine hydrochloride. Component (c) the emulsifying agent, is used in the invention in a weight ratio relative to amantadine hydrochloride of about 0.03 to 0.05 and preferably about 0.04.

For the low wax formula, the normal dose of amantadine hydrochloride is 100 mg. Component (b) the suspending vehicle, is used in the invention in a weight ratio relative to amantadine hydrochloride of about 0.75 to 1.45 and preferably about 1.10. Component (c) the emulsifying agent, is used in a weight ratio relative to amantadine hydrochloride of about 0.03 to 0.05 and preferably about 0.04.

For the purpose of this invention, the weight ratio of suspending vehicle to amantadine described above, is calculated using the formula:

$$\frac{\text{weight of suspending vehicle}}{\text{weight of solid to be suspended}} = \text{Base Absorption}$$

wherein: Base Absorption means an adequate amount of viscosity to provide content uniformity and ease of processing; suspending vehicle includes all components soluble in the primary vehicle, such that the mixture becomes the suspending vehicle; and solid to be suspended means all components that are not soluble make up the solid phase.

An example calculation of the weight ratio for a no wax formulation is provided below:

$$\frac{\text{(wght) soybean oil} + \text{(wght) lecithin}}{\text{(wght) solid to be suspended}}$$

An example calculation of the weight ratio for a low wax formulation is provided below:

$$\frac{\text{(wght)soybean oil} + \text{(wght)lecithin} + \text{(wght)vegetable shortening}}{\text{(wght) solid to be suspended}}$$

Additional optional excipients may be used to adjust flow and suspension (settling) characteristics as needed. Such optional excipient should be insoluble in the soybean oil the main constituent of the liquid suspending vehicle and may be materials, such as, but not limited to, titanium dioxide, silicon dioxide calcium carbonate, calcium phosphate, magnesium carbonate, calcium and magnesium oxide and kaolin.

In addition, other excipients such as flavoring agents, color additives or other excipients known to those skilled in the art may be used in the present invention.

The no wax pharmaceutical compositions of the invention are prepared by mixing the above listed components (a), (b), (c) and optionally (d) in any order although it is preferred to first mix the suspending vehicle (b) (i.e., soybean oil) and the emulsifying agent (c) (i.e., lecithin) and then to add the desired amount of amantadine hydrochloride (a) followed by (d) additional optional excipients.

The low wax pharmaceutical compositions of the invention are prepared by mixing the above listed components (a), (b), (c) and optionally (d) in any order although it is preferred to first mix the suspending vehicle (b) (i.e., soybean oil) and the previously melted wax or lipid (i.e., vegetable shortening) and the emulsifying agent (c) (i.e., lecithin), such mixture being allowed to cool to about 100° F. before adding the amantadine hydrochloride (a), followed by (d) additional optional excipients.

Such prepared compositions are then used to fill hard or soft gelatin capsules. A soft gelatin capsule is preferred in view of the ease of storage and availability in a wide variety of shapes and sizes. Technology for forming soft gelatin capsules is described in detail in the chapter entitled "Soft Gelatin Capsules" by J. P. Stanley, at pages 359-384 of "The Theory and Practice of Industrial Pharmacy", by Leon Lachman, Herbert A. Lieberman and Joseph L. Kanig Lea & Febiger, Philadelphia (1970). Soft gelatin capsules may be manufactured as known in the art, e.g., as described in U.S. Pat. No. 4,744,988 (R. P. Scherer Corporation).

It has been unexpectedly found that the no wax and low wax formulations of the present invention significantly enhance the dissolution rate of amantadine hydrochloride per unit dose. In addition, the content uniformity of the unit dose is maintained in the absence of the high melting point waxes traditionally used in the formulation of this product.

Further details, typical embodiments of the oral preparations and of the processes for preparing same are illustrated in further detail in the following examples.

EXAMPLE 1

| Symmetrel ® No Wax Formulation | |
|---|---|
| Ingredients | mg/capsule |
| Amantadine HCL | 100.0 |
| Lecithin, Unbleached | 4.0 |
| Soybean Oil, USP | 103.9 |
| Theoretical Fill Weight | 207.0 |

The Soybean Oil, USP (103 mg/capsule) was added to a mixing tank. While stirring, the lecithin (4 mg/capsule) was added, this mixture was stirred for about 15 minutes or until uniform. While stirring the above mixture, amantadine hydrochloride (100 mg/capsule) was added in small portions, each small portion being thoroughly wetted prior to addition of the next portion, thus forming a suspension. The suspension was then passed through a mill to deaggregate the particles and deaerated by methods known to those skilled in the art. Prior to encapsulation, the mixture was carefully restirred for about 15-20 minutes so as not to incorporate air into the mixture. The mixture was then encapsulated in soft gelatin capsules, each capsule containing 100 mg of amantadine HCL.

Pilot scale batches of no wax Symmetrel ® capsules were manufactured. These capsules were not used for commercial purposes but demonstrated the feasibility of the formulas and procedures.

Assays Performed on the Capsules

Testing was performed on capsule samples taken during the manufacturing process described above. Analysis of the capsules were obtained using the USP assay method (non-aqueous titration). Results of the dissolution test used USP methodology and met USP criteria for the product. Results are shown in Tables I and II.

The soybean oil (103 mg/capsule) was added to a mixing tank, while stirring, the vegetable shortening (8 mg/capsule) was added, the vegetable shortening having been previously heated to about 38° C. (100.4° F.). To this was added, while stirring, lecithin (4 mg/capsule). This mixture was stirred until uniform, and at such time the temperature was recorded. (If the temperature is over 100° F., it must be allowed to cool to 100° F.).

After cooling, if such is necessary, and while stirring the mixture from above, small portions of amantadine hydrochloride were added such that each portion was thoroughly wetted prior to the addition of the next portion of amantadine hydrochloride. This mixture was then mixed for about 15 minutes or until uniform. The uniform mixture was then milled to deaggregate the particles and then deaerated. Prior to encapsulation the mixture was restirred for about 20 minutes such that no air was incorporated into the mixture.

Pilot scale batches of low wax Symmetrel ® capsules were manufactured. These capsules were not used for commercial purposes but demonstrated the feasibility of the formulas and procedures.

Assays Performed on the Capsules

Testing was performed on capsule samples taken during the manufacturing process described above. Analysis of the low wax capsules were obtained using the USP assay method (non-aqueous titration). Results of the dissolution test used USP methodology and met USP criteria for the product. Results are shown in Tables II and IV.

TABLE I

DISSOLUTION* OF 'NO WAX' SYMMETREL ® 100 MG CAPSULES

| Sample | No. Tested | Mean ± SD Percent Dissolved Time (Minutes) | | | | | Meets USP Specs (Q = 75% in 45 min) |
|---|---|---|---|---|---|---|---|
| | | 15 | 30 | 45 | 60 | 120 | |
| Beginning | 6 | 40.0 ± 2.3 | 76.4 ± 2.9 | 88.5 ± 3.9 | 95.0 ± 3.6 | 101.8 ± 1.1 | $S_1$ |
| Middle | 12 | 40.0 ± 3.8 | 74.7 ± 4.0 | 88.2 ± 5.3 | 94.9 ± 4.4 | 100.9 ± 1.0 | $S_2$ |
| End | 6 | 41.4 ± 2.8 | 77.6 ± 3.2 | 91.8 ± 3.4 | 98.3 ± 3.0 | 100.8 ± 0.9 | $S_1$ |

*USP method using Apparatus 1 (baskets) at 100 RPM and 900 mls of distilled water at 37° C.

TABLE II

CONTENT UNIFORMITY OF "NO WAX SYMMETREL ® 100 mg CAPSULES

| | mg/Capsule | | |
|---|---|---|---|
| Sample No. | Beginning | Middle | End |
| 1 | 99.0 | 99.7 | 98.7 |
| 2 | 98.7 | 99.1 | 99.4 |
| 3 | 99.8 | 97.0 | 100 |
| 4 | 98.6 | 99.2 | 100 |
| 5 | 98.9 | 99.5 | 99.3 |
| 6 | 99.8 | 97.5 | 100 |
| Mean ± % RSD | 99.1 ± 0.5% | 98.7 ± 1.1% | 99.6 ± 0.5% |
| Grand Mean | | 99.1 ± 0.8% RSD | |

TABLE III

DISSOLUTION* OF 'LOW WAX' SYMMETREL ® 100 MG CAPSULES

| Sample | No. Tested | Mean ± SD Percent Dissolved Time (Minutes) | | | | | Meets USP Specs (Q = 75% in 45 min) |
|---|---|---|---|---|---|---|---|
| | | 15 | 30 | 45 | 60 | 120 | |
| Beginning | 6 | 41.6 ± 7.8 | 74.6 ± 9.1 | 90.9 ± 4.6 | 96.3 ± 3.4 | 99.8 ± 1.0 | $S_1$ |
| Middle | 6 | 43.5 ± 5.9 | 74.0 ± 4.9 | 89.8 ± 3.6 | 95.6 ± 4.2 | 98.5 ± 5.3 | $S_1$ |
| End | 12 | 41.3 ± 12.6 | 73.2 ± 8.1 | 87.3 ± 7.3 | 93.8 ± 6.1 | 97.3 ± 1.1 | $S_2$ |

*USP method using Apparatus 1 (baskets) at 100 RPM and 900 mls of distilled water at 37° C.

(n = 18) ± % RSD

EXAMPLE 2

Symmetrel ® Low Wax Formulas

| Ingredients | mg/capsule |
|---|---|
| Soybean Oil, USP | 103.0 |
| Lecithin | 4.0 |
| Amantadine HCL | 100.0 |
| Vegetable Shortening | 8.0 |
| Theoretical capsule fill weight | 215.0 |

TABLE IV

CONTENT UNIFORMITY OF "LOW WAX SYMMETREL ® 100 mg CAPSULES

| | mg/Capsule | | |
|---|---|---|---|
| Sample No. | Beginning | Middle | End |
| 1 | 97.1 | 97.6 | 94.8 |
| 2 | 96.4 | 97.7 | 97.0 |
| 3 | 96.2 | 97.4 | 97.3 |
| 4 | 97.4 | 97.3 | 95.7 |
| 5 | 96.4 | 97.5 | 95.0 |
| 6 | 96.1 | 97.5 | 94.4 |
| Mean ± % RSD | 96.6 ± 0.5% | 97.5 ± 0.1% | 95.7 ± 1.3% |
| Grand Mean | | 96.6 ± 1.1% RSD | |

TABLE IV-continued
CONTENT UNIFORMITY OF "LOW WAX SYMMETREL ® 100 mg CAPSULES

| Sample No. | mg/Capsule | | |
|---|---|---|---|
| | Beginning | Middle | End |
| (n = 18) ± % RSD | | | |

What is claimed is:

1. A pharmaceutical dosage form which comprises a soft gelatin capsule for oral administration containing in the hollow interior thereof, a pharmaceutical composition comprising a suspension of the following components:
   (a) a therapeutically effective amount of amantadine hydrochloride;
   (b) a suspending vehicle including a low melting point of wax or lipid or a combination thereof together with a primary vehicle consisting essentially of soybean oil, peanut oil, sesame oil, cottonseed oil, corn oil, sunflower oil, olive oil, safflower oil, or coconut oil, and comprising no greater than 10% of the capsule fill weight;
   (c) at least one emulsifying agent; and
   (d) optionally including additional pharmaceutically acceptable excipients.

2. The dosage form of claim 1 wherein the amantadine hydrochloride is present in an amount of about 100 mg/capsule.

3. The dosage form of claim 2 wherein the low melting point wax or lipid or combination thereof, of component (b) is present in a weight ratio relative to amantadine hydrochloride of about 0.75 to 1.45.

4. The dosage form of claim 3 wherein the low melting point wax or lipid or combination thereof, of component (b) is present in a weight ratio relative to amantadine hydrochloride of about 1.10.

5. The dosage form of claim 2 wherein component (c) is present in a weight ratio relative to amantadine hydrochloride of about 0.03 to 0.05.

6. The dosage form of claim 5 wherein component (c) is present in a weight ratio relative to amantadine hydrochloride of about 0.04.

7. The dosage form of claim 2 wherein the low melting point wax or lipid or combination thereof, of component (b) is present in a weight ratio relative to amantadine hydrochloride of about 0.75 to 1.45 and component (c) is present in a weight ratio relative to amantadine hydrochloride of about 0.03 to 0.05.

8. The dosage form of claim 7 wherein the low melting point wax or lipid or combination thereof, of component (b) is present in a weight ratio relative to amantadine hydrochloride of about 1.10 and component (c) is present in a weight ratio relative to amantadine hydrochloride of about 0.04.

9. The dosage form of claim 1 wherein the component (b) is a mixture of at least one primary vehicle selected from the group consisting of edible oils such as soybean oil, sunflower oil, olive oil, coconut oil, peanut oil, sesame oil, cottonseed oil, corn oil and safflower oil and at least one low melting point wax or lipid or a combination thereof, selected from the group consisting of vegetable shortening, cocoa butter, margarine, Hard fat NF, butter and partially hydrogenated oil.

10. The dosage form of claim 3 wherein the component (b) is a mixture of at least one primary vehicle selected from the group consisting of edible oils such as soybean oil, sunflower oil, olive oil, coconut oil, peanut oil, sesame oil, cottonseed oil, corn oil and safflower oil and at least one low melting point wax or lipid or combination thereof selected from the group consisting of vegetable shortening, cocoa butter, margarine, hard fat NF, butter and partially hydrogenated oil.

11. The dosage form of claim 4 wherein component (b) is a mixture of at least one primary vehicle selected from the group consisting of edible oils such as soybean oil, sunflower oil, olive oil, coconut oil, peanut oil, sesame oil, cottonseed oil, corn oil and safflower oil and at least one low melting point wax or lipid or a combination thereof selected from the group consisting of vegetable shortening, cocoa butter, margarine, hard fat NF, butter and partially hydrogenated oil.

12. The dosage form of claim 9 wherein component (b) is a mixture of soybean oil and vegetable shortening.

13. The dosage form of claim 10 wherein component (b) is a mixture of soybean oil and vegetable shortening.

14. The dosage form of claim 11 wherein component (b) is a mixture of soybean oil and vegetable shortening.

15. The dosage form of claim 1 wherein component (c) is selected from the group consisting of lecithin, polysorbate 20, 40, 60 and 80.

16. The dosage form of claim 5 wherein component (c) is selected from the group consisting of lecithin, polysorbate, 20, 40, 60 and 80.

17. The dosage form of claim 6 wherein component (c) is selected from the group consisting of lecithin, polysorbate, 20, 40, 60 and 80.

18. The dosage form of claim 7 wherein component (c) is selected from the group consisting of lecithin, polysorbate, 20, 40, 60 and 80.

19. The dosage form of claim 8 wherein component (c) is selected from the group consisting of lecithin, polysorbate, 20, 40, 60 and 80.

20. The dosage form of claim 15 wherein component (c) is lecithin.

21. The dosage form of claim 16 wherein component (c) is lecithin.

22. The dosage form of claim 17 wherein component (c) is lecithin.

23. The dosage form of claim 18 wherein component (c) is lecithin.

24. The dosage form of claim 19 wherein component (c) is lecithin.

25. A method for producing a dosage form of claim 1 comprising:
   (a) adding to the primary vehicle, heated low melting point wax or lipid and the emulsifying agent;
   (b) allowing the mixture of (a) to cool to less than or equal to 100° F.;
   (c) adding to the mixture of step (b) amantadine HCL; and
   (d) encapsulating the mixture of step (c) in a soft gelatin capsule.

* * * * *